(12) United States Patent
Krumeich et al.

(10) Patent No.: US 10,695,311 B2
(45) Date of Patent: *Jun. 30, 2020

(54) SOLUTION FOR OPHTHALMOLOGY

(71) Applicant: Joerg H. Krumeich, Bochum (DE)

(72) Inventors: Joerg H. Krumeich, Bochum (DE); Gerrit Nattler, Dorsten (DE)

(73) Assignee: Jörg H. Krumeich, Bochum (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/268,156

(22) Filed: Feb. 5, 2019

(65) Prior Publication Data

US 2019/0167621 A1 Jun. 6, 2019

Related U.S. Application Data

(63) Continuation of application No. 15/172,633, filed on Jun. 3, 2016, now Pat. No. 10,220,012.

(51) Int. Cl.
| | |
|---|---|
| *A61K 31/198* | (2006.01) |
| *A61K 9/08* | (2006.01) |
| *A61K 9/00* | (2006.01) |
| *A61K 47/36* | (2006.01) |

(52) U.S. Cl.
CPC .......... *A61K 31/198* (2013.01); *A61K 9/0048* (2013.01); *A61K 9/0051* (2013.01); *A61K 9/08* (2013.01); *A61K 47/36* (2013.01)

(58) Field of Classification Search
CPC .. A61K 31/198; A61K 9/0048; A61K 9/0051; A61K 9/08; A61K 47/36
See application file for complete search history.

(56) References Cited

U.S. PATENT DOCUMENTS

| | | | |
|---|---|---|---|
| 5,182,300 | A | 1/1993 | Pellegata |
| 10,220,012 | B2 * | 3/2019 | Krumeich ............ A61K 31/198 |
| 2004/0072809 | A1 | 4/2004 | Demopulos |
| 2005/0191322 | A1 | 9/2005 | Norrby |
| 2006/0004089 | A1 | 1/2006 | Pinza |
| 2017/0135972 | A1 | 5/2017 | Muthukumar |

FOREIGN PATENT DOCUMENTS

| | | |
|---|---|---|
| CN | 1762350 A | 4/2006 |
| CN | 1985801 A | 6/2007 |
| DE | 100 58 164 A1 | 5/2002 |
| DE | 10 2012 020 045 A1 | 8/2013 |

OTHER PUBLICATIONS

Winblade et al., Journal of Biomedical Research (2002), 56(4), pp. 618-631.

* cited by examiner

*Primary Examiner* — Joseph R Kosack
(74) *Attorney, Agent, or Firm* — Dickinson Wright PLLC

(57) ABSTRACT

The invention relates to a solution for lysis of particles and fibers that adhere to a lens capsule of the eye during cataract operations, which solution contains 0.5-3.5 wt.-% lysine, particularly L-lysine, in an isotonic to hypertronic aqueous solution.

23 Claims, No Drawings

SOLUTION FOR OPHTHALMOLOGY

This application is a continuation of U.S. patent application Ser. No. 15/172,633, filed on Jun. 3, 2016, which is incorporated by reference in its entirety.

The invention relates to a solution for lysis of particles and fibers that adhere to a lens capsule of the eye during cataract operations.

Cataract or cataract is a disease of the eye in which clouding of the lens occurs, resulting in reduced ability to see.

Nowadays, in the treatment of cataract (cataract), generally the lens with the capsule is no longer removed (intracapsular cataract extraction); instead, an opening is introduced into the anterior capsule. Subsequently, the lens core and the subcapsular posterior cortex layers are broken down using ultrasound (phacoemulsification) and suctioned away using a suctioning/flushing apparatus (irrigation/aspiration). In this type of procedure, the lens capsule is maintained, so that the new lens can be fixed in place and the separation between anterior and posterior compartment can be maintained.

The operation consists of 1. fracturing of the lens core, using a handpiece that emits ultrasound and suctions off the particles, 2. after removal of the core, the lens residues—corex and epinucleus—must be suctioned away out of the capsule. This second procedure of suctioning—irrigation/aspiration—of the firmly adhering tissue material leads to tensile stresses on the entire suspension of the lens capsule, namely the zonula fibers, which reach circularly into the capsule, in spider-like manner.

Depending on the state of the zonula fibers, the capsule can be luxated out of its suspension within the irrigation/aspiration procedure, without the surgeon noticing that this has happened. What are called toric lenses, which correct cornea curvature, and multi-focal lenses lose their effect because they are then displaced eccentrically, or exert undesirable refractions of the light, which spoil the operation result. Subsequently to removal of the cloudy lens, what is called a posterior-chamber lens is generally applied to replace the cloudy lens. A prerequisite for this is maintaining the capsule diaphragm, which has been freed of all lens components. In order to ensure complete operation success, it is necessary that the posterior capsule that is left in place is completely clear.

The eye lens is an elastic, biconvex body. A single-layer cubic epithelium is situated on the anterior surface of the lens; its cells proliferate and migrate to the sides, what is called the lens equator. After the lens capsule has been opened during an operation to remove the cataract, the cells can migrate from the equator edge to the inside of the capsule. The epithelial cells or lens fibers are anchored in the lens capsule by means of hemidesmosomes.

The natural lens is suspended on the ciliary body by what are called zonula fibers, wherein the zonula fibers reach into the lens capsule. The lens situated behind the iris, the zonula fibers, and the iris divide the interior of the eye into an anterior compartment and a posterior compartment.

Conventionally, the remaining capsule is mechanically polished before implantation of the posterior-chamber lens, in order to release any remaining lens fibers from the capsule. However, the mechanical procedure of polishing has the disadvantage that it is not thorough enough to remove all the cells that still adhere to the capsule, so that after completion of the operation, what is called capsule fibrosis can occur as the result of proliferation and migration of these cells from the lens equator and from the outside of the lens capsule; this results in renewed clouding (called secondary cataract). This secondary cataract must then be removed within the scope of a further operation or by means of laser treatment.

For prophylaxis of capsule fibrosis, it was proposed in DE 100 58 164 A1 to carry out cleaning of the posterior lens capsule by means of application of a solution of α-chymotrypsin in great dilution, instead of mechanical polishing. In this regard, the chymotrypsin solution is used as a flushing solution, for example, after removal of the lens core and posterior lens layers, over a period of action from 30 s to 1.5 min, in order to release any remaining epithelial cells from the lens capsule, in that the protein components of the hemidesmosomes, which anchor the epithelial cells to the lens capsule, are digested. It was possible to extensively preclude splitting of the protein components of the lens capsule itself by means of the selection of a very low chymotrypsin concentration.

A chymotrypsin solution in a viscoelastic liquid for prophylaxis of capsule fibrosis is known from DE 10 2012 020 045 A1.

However, it has proven to be problematical in the past that chymotrypsin solutions are not easy to handle, because of the great enzymatic activity.

The invention is therefore based on the task of making available a composition in which an alternative means is used.

This task is accomplished, according to the invention, by means of a solution that contains 0.5-3.5 wt.-% lysine, particularly L-lysine, in an isotronic to hypertonic aqueous solution.

Lysine is a diaminohexanoic acid. To the extent that diaminohexanoic acids have similar properties, they are understood to be included in the term "lysine" used here. In particular, however, L-lysine is a possibility, also in a mixture with D-lysine (racemate).

In the following, the invention will be described with reference to L-lysine.

It is understood that lysine can be used in any physiologically tolerated form, particularly in the form of its physiologically tolerated salts. In particular, hydrochloride is a possibility here.

The aqueous solution preferably contains 1-3 wt.-% lysine as hydrochloride. Primarily, an aqueous solution is understood to be a saline solution, the tonicity of which is determined by the saline content and the lysine content. It is understood that other additives can also be used to adjust the tonicity, for example boric acid.

The osmolarity of the aqueous solution particularly corresponds to that of a 0.9-1.7% saline solution, taking the lysine content into consideration.

It is practical if the solutions according to the invention have a pH of 6-8.

Furthermore, the solutions according to the invention can also be adjusted to be viscoelastic, in order to guarantee uniform wetting of the lens capsule.

Viscoelastic liquids are non-Newtonian fluids. While in the case of Newtonian fluids, viscosity is a constant at a given temperature, in the case of viscoelastic fluids the viscosity changes as a function of the shear velocity. In particular, the viscosity can decrease with an increasing shear velocity; in these cases, one speaks of pseudoplastic or structure-viscous behavior. In general, such fluids contain elongated molecules that orient themselves, relative to one another, at high velocity gradients, in such a manner that they slide past one another more easily. Furthermore, the case is also known that a fluid becomes more rigid at an increasing deformation velocity.

The viscoelastic fluid is an aqueous solution and, as a polymer, can particularly contain a polysaccharide, which can be hyaluronic acid, chondroitin sulfate, methylcellulose and/or hydroxypropyl methylcellulose. The compounds can, of course, also be present in the form of the corresponding salt. Hyaluronic acid is particularly preferred. Hyaluronic acid is a glycosaminoglycan with disaccharide repetition units composed of glucuronic acid and N-acetyl-glucosamine. Non-animal, stabilized hyaluronic acid (NASHA) can also be involved. The fluid can contain not only hyaluronic acid but also chondroitin sulfate.

The solution according to the invention is supposed to be used, above all, during surgical treatment of a cataract, for easier removal of the tissue parts that surround the core, the aspiration of which parts can lead to the problems with the entire lens suspension described above.

Furthermore, the solution according to the invention is also supposed to contribute to removal of epithelial cells from the capsule.

The solution according to the invention softens the lens residues to be suctioned away, so that the significantly lower tensile forces during aspiration of these lens residues cannot lead to luxation of zonula fibers and therefore not to displacement of the entire capsule.

By means of careful removal of epithelial cells, capsule fibrosis is prevented; this results in renewed clouding of the lens and occurs, in part, with mechanical removal of the epithelial cells. In contrast to the use of chymotrypsin in a physiological saline solution, as described in DE 100 58 164 A1, complete filling and wetting of the entire capsule sac and therefore uniform removal of the epithelial cells to be removed, and, if necessary, of other protein components, is achieved when using a viscoelastic fluid.

The concentrations are based on the finding that a solution of L-lysine in the said concentration or dilution is sufficient, on the one hand, for decomposing the protein components of the hemidesmosomes greatly enough so as to dissolve the bond with the remaining cells, but on the other hand does not lead to damage of the lens capsule. While under some circumstances, digestion of not only the hemidesmosomes but also of the lens capsule can occur in the case of digestion with a chymotrypsin solution, studies by the inventor have shown that when using lysine solutions having a lower concentration, damage to the lens capsule does not occur, whereas digestion of the hemidesmosomes still takes place to a sufficient extent, in order to remove any cells that might remain, so that these can be flushed away during the flushing procedure.

Experiments on donor eyes, the corneas of which were used for cornea transfers, showed that when using L-lysine in the concentration indicated above, neither the zonula fibers nor the posterior capsule are attacked. Furthermore, surgical studies within the scope of extracapsular procedures showed that when using L-lysine concentrations of up to 5%, the lens capsule remained intact during and after the procedure, and that it was possible to prevent capsule fibrosis after the procedures. The surgical result is therefore permanent; further procedures for treatment of possible capsule fibrosis are rarely or never necessary. The solution according to the invention can be used with every phacoemulsification, with or without lens implantation, to clean the posterior capsule. In this regard, the solution according to the invention can be produced from commercially available L-lysine. In particular, the solution can be present as a flushing solution.

When performing the extracapsular operation, it has proven to be practical to apply 1 to 5 ml of the L-lysine according to the invention to the posterior capsule after removal of the cloudy lens core and the subcapsular cortex layer (Cortex lentis), using an anterior-chamber cannula. After a sufficient period of action, the solution is suctioned away and rinsed off. In this regard, the period of action is primarily dependent on the concentration of the solution. For a solution with a concentration of 2 wt.-%, it lies between 30 s and 5 min, preferably at approximately 1 min. The period of action should not amount to more than 5 min, preferably not more than 3 min.

The viscosity of the viscoelastic solvent preferably amounts (at a shear velocity of 0) to at least 10,000 mPa s, particularly preferably at least 100,000 mPa s, and very particularly preferably at least 1,000,000 mPa s. Hyaluronic acid solutions have fundamentally become known within the scope of cataract treatment, but have not been used until now as solvents for L-lysine for removal of epithelial cells from the lens capsule. Until now, the applications were spreading of the anterior chamber and of the capsule during implantation of the artificial lens, for example. Known viscoelastic solutions are, for example, Healon®, Healon 5®, and Healon GV® from Abbott Medical Optics, or Viscoat® and ProVisc® from Alcon. Healon® has a viscosity of 300,000 mPa s and a molecular mass of the hyaluronic acid of 4 million Dalton; Healon GV® has a viscosity of 3,000,000 mPa s and a molecular mass of the hyaluronic acid of 5 million Dalton, and Healon 5® has a viscosity of 7,000,000 mPa s and a molecular mass of the hyaluronic acid of 4 million Dalton. At a high shear velocity, for example in the case of injection from a syringe, in contrast, the viscosity clearly decreases.

The concentration of the polysaccharide, which can particularly be hyaluronic acid, in the solution typically amounts to 0.5 to 5 wt.-%, particularly 1 to 3 wt.-%. The polysaccharide is usually dissolved in a physiological solvent; for example, the solvent can contain sodium chloride, potassium chloride and/or calcium chloride in water. An example is what is called Ringer solution. Furthermore, the solvent can contain a pH buffer, for example a combination of hydrogen phosphate salt and dihydrogen phosphate salt, e.g. the corresponding sodium salt.

The invention claimed is:

1. A method for facilitating removal of lens cortex tissue from a lens capsule of an eye of a patient during a cataract operation, the method comprising:
    applying a solution containing 0.5-3.5 wt.-% lysine in an isotonic to hypertonic aqueous solution to the lens capsule during the cataract operation; and
    aspirating the lens cortex tissue and solution from the lens capsule.

2. The method according to claim 1, wherein the lysine is present in the form of a physiologically tolerated salt.

3. The method according to claim 1, wherein the solution contains 1-3 wt.-% lysine hydrochloride.

4. The method according to claim 1, wherein the solution is a saline solution.

5. The method according to claim 1, wherein the osmolarity of the solution corresponds to that of a 0.9-1.7% saline solution.

6. The method according to claim 1, wherein the solution has a pH of 6-8.

7. The method according to claim 1, wherein the solution is viscoelastic.

8. The method according to claim 7, wherein the solution contains a polysaccharide.

9. The method according to claim 1, wherein epithelial cells and protein components are also removed from the lens capsule.

10. The method according to claim 1, wherein said method achieves prophylaxis of capsular fibrosis.

11. The method according to claim 1, wherein the lysine is L-lyisne.

12. The method according to claim 1, wherein the lens tissue and solution are aspirated from the lens capsule between 30 seconds and 3 minutes after application of the solution to the lens capsule.

13. A method for preventing capsule fibrosis or secondary cataract in a lens capsule after a cataract operation, the method comprising:
applying a solution containing 0.5-3.5 wt.-% lysine in an isotonic to hypertonic aqueous solution to the lens capsule during the cataract operation; and
aspirating the solution from the lens capsule.

14. The method according to claim 13, wherein the lysine is present in the form of a physiologically tolerated salt.

15. The method according to claim 13, wherein the solution contains 1-3 wt.-% lysine hydrochloride.

16. The method according to claim 13, wherein the solution is a saline solution.

17. The method according to claim 13, wherein the osmolarity of the solution corresponds to that of a 0.9-1.7% saline solution.

18. The method according to claim 13, wherein the solution has a pH of 6-8.

19. The method according to claim 13, wherein the solution is viscoelastic.

20. The method according to claim 19, wherein the solution contains a polysaccharide.

21. The method according to claim 13, wherein epithelial cells and protein components are removed from the lens capsule.

22. The method according to claim 13, wherein the lysine is L-lyisne.

23. The method according to claim 13, wherein the solution is aspirated from the lens capsule between 30 seconds and 3 minutes after application of the solution to the lens capsule.

* * * * *